(12) United States Patent
Rogers et al.

(10) Patent No.: US 8,103,524 B1
(45) Date of Patent: Jan. 24, 2012

(54) PHYSICIAN RECOMMENDATION SYSTEM

(75) Inventors: Lisa H. Rogers, Palo Alto, CA (US); Bindu Gakhar, San Francisco, CA (US); Srinivas Singampalli, Newark, CA (US); Safia A. Ali, San Francisco, CA (US)

(73) Assignee: Intuit Inc., Mountain View, CA (US)

( * ) Notice: Subject to any disclaimer, the term of this patent is extended or adjusted under 35 U.S.C. 154(b) by 476 days.

(21) Appl. No.: 12/323,330

(22) Filed: Nov. 25, 2008

(51) Int. Cl.
*G06Q 50/00* (2006.01)
(52) U.S. Cl. .......................................................... 705/2
(58) Field of Classification Search .................... 705/2, 3
See application file for complete search history.

(56) References Cited

U.S. PATENT DOCUMENTS

| | | | |
|---|---|---|---|
| 7,085,806 B1* | 8/2006 | Shapira | 709/203 |
| 2006/0046854 A1* | 3/2006 | Arevalo Baeza et al. | 463/42 |
| 2006/0161456 A1* | 7/2006 | Baker et al. | 705/2 |
| 2007/0067185 A1* | 3/2007 | Halsted | 705/2 |
| 2007/0179811 A1* | 8/2007 | Reiner | 705/2 |
| 2008/0046286 A1* | 2/2008 | Halsted | 705/2 |
| 2008/0167998 A1* | 7/2008 | Hyte | 705/80 |
| 2008/0270230 A1* | 10/2008 | Hendrickson et al. | 705/14 |

* cited by examiner

*Primary Examiner* — Gerald J. O'Connor
*Assistant Examiner* — Edward Winston, III
(74) *Attorney, Agent, or Firm* — Osha • Liang LLP

(57) ABSTRACT

A method for recommending a physician, comprising obtaining user feedback for the physician prior to obtaining a plurality of search criteria, obtaining the plurality of search criteria specifying physician expertise, identifying a plurality of physicians based on a search of the plurality of search criteria, wherein the search is performed on a user generated physician expertise data set, performing a comparison of the plurality of physicians, and displaying a recommendation for one of the plurality of physicians based on the comparison.

30 Claims, 6 Drawing Sheets

PHYSICIAN RECOMMENDATION SYSTEM

BACKGROUND

The process of choosing a healthcare provider is currently time consuming and tedious. Patients may unsuccessfully meet and spend time with multiple physicians until one is found that suits the patient's specific needs. A variety of factors exist that patients tend to consider when choosing a physican, and these factors are not uniform across all patients. Often, patients do not have enough information upon which to base a decision. In this very personal choice, more physician data leads to more informed decisions, which ultimately leads to better patient care.

Current physician finder services often provide relatively scant information and typically depend on ranking systems based on ratings. Further, many physician finder systems use rankings based in large part on physician credentials and information of a non-qualitative nature. Information based on experiences of other patients with physicians may provide patients with a much richer framework for making informed decisions.

SUMMARY

In general, in one aspect, the invention relates to a method for recommending a physician, comprising obtaining user feedback for the physician prior to obtaining a plurality of search criteria, obtaining the plurality of search criteria specifying physician expertise, identifying a plurality of physicians based on a search of the plurality of search criteria, wherein the search is performed on a user generated physician expertise data set, performing a comparison of the plurality of physicians, and displaying a recommendation for one of the plurality of physicians based on the comparison.

In general, in one aspect, the invention relates to a system for recommending a physician, comprising a processor, a memory operatively connected to the processor, and a physician recommendation system resident in memory and configured to obtain user feedback for the physician prior to obtaining a plurality of search criteria, obtain the plurality of search criteria specifying physician expertise, identify a plurality of physicians based on a search of the plurality of search criteria, wherein the search is performed on a user generated physician expertise data set, perform a comparison of the plurality of physicians, and display a recommendation for one of the plurality of physicians based on the comparison.

In general, in one aspect, the invention relates to a computer readable medium storing instructions to recommending a physician, the instructions comprising functionality to obtain user feedback for the physician prior to obtaining a plurality of search criteria, obtain the plurality of search criteria specifying physician expertise, identify a plurality of physicians based on a search of the plurality of search criteria, wherein the search is performed on a user generated physician expertise data set; perform a comparison of the plurality of physicians, and display a recommendation for one of the plurality of physicians based on the comparison.

Other aspects and advantages of the invention will be apparent from the following description and the appended claims.

DETAILED DESCRIPTION

Figure 1:
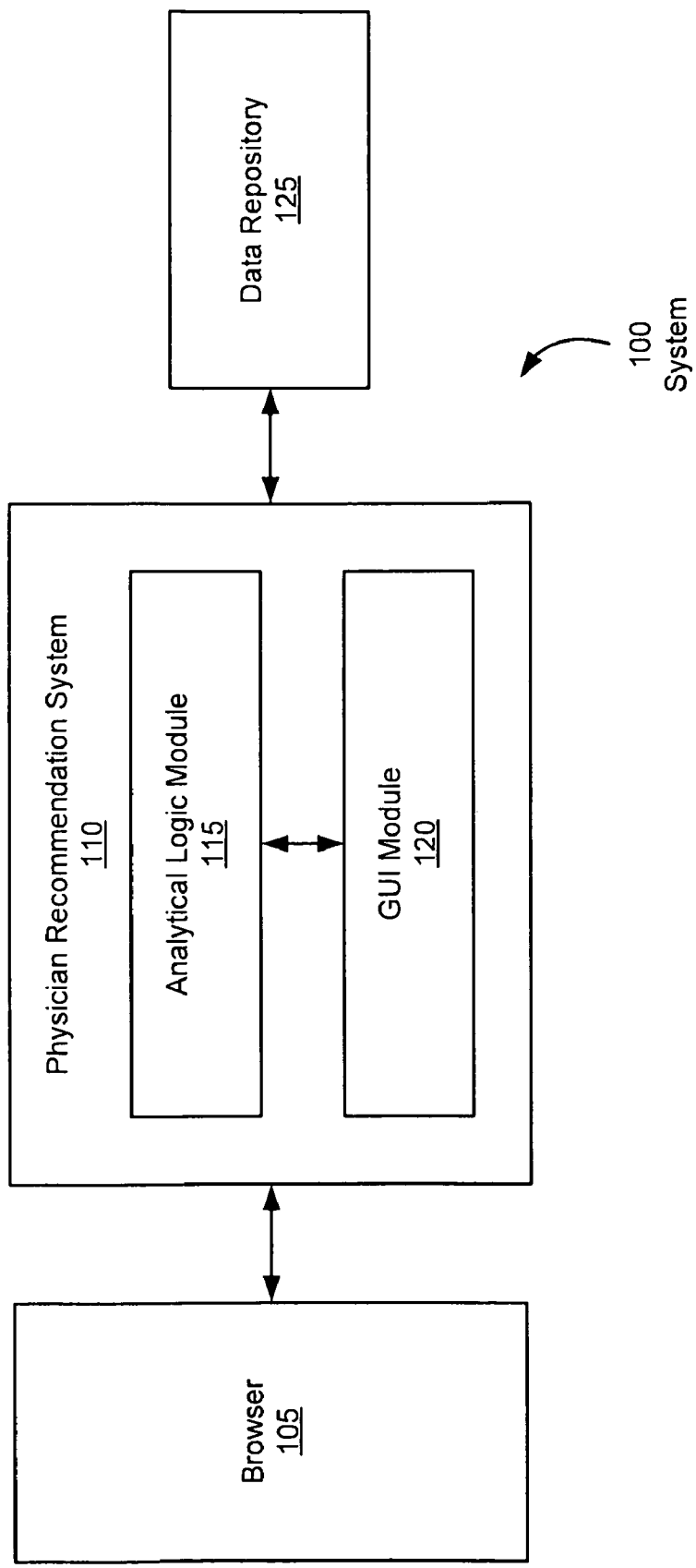
FIG. 1 shows a data flow diagram of a system in accordance with one or more embodiments of the invention.

Specific embodiments of the invention will now be described in detail with reference to the accompanying figures. Like elements in the various figures are denoted by like reference numerals for consistency.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention provide a system and method for recommending a physician based on user generated content. In general, embodiments of the invention provide a system and method for creating a recommendation based on experiences with a physician. In general, embodiments of the invention provide a system and method for comparing physicians to choose one best suited for an individual's needs.

FIG. 1 shows a system (100) in accordance with one or more embodiments of the invention. As shown in FIG. 1, the system (100) includes multiple components such as a browser (105), a physician recommendation system (110), and a data repository (125). These components are described below and may be located on the same device (e.g. a server, mainframe, desktop Personal Computer (PC), laptop, Personal Digital Assistant (PDA), telephone, mobile phone, kiosk, cable box, and any other device) or may be located on separate devices connected by a network (e.g. the Internet), with wired and/or wireless segments. Those skilled in the art will appreciate that there may be more than one data repository and physician recommendation system running on a device, as well as more than one browser interfacing with various components.

In one or more embodiments of the invention, a browser (105) is configured to display a graphical user interface (GUI) associated with the physician recommendation system (110). Those skilled in the art, having benefit of this detailed description, will appreciate that there will be many ways in which a GUI may be viewed other than using a browser.

In one or more embodiments of the invention, a physician recommendation system (110) contains an analytical logic module (115) and a GUI module (120). The physician recommendation system (110) is configured to recommend a physician to a user based on existing user data. The GUI module (120) is configured to enable a GUI for display in the browser (105). The analytical logic module (115) is configured to create recommendations for physicians based on user data.

The physician recommendation system (110) may be used for identifying a general physician based on specific search criteria, identifying a specialist based on specific search criteria, identifying a physician that is part of a specific practice, asking another user of their opinion of a specific physician, scheduling an appointment with a physician, providing feedback on a specific physician after having an appointment with him/her, and providing other users with general recommendations on physicians seen in the past.

The physician recommendation system (110) may also be associated with a financial application in that the financial application is a data source and/or input source for the system (100). Those skilled in the art, having benefit of this detailed description, will appreciate that there will be many other uses for the physician recommendation system (110), and that the physician recommendation system (110) may be applied to recommendations for other professional services (e.g. restaurants, lawyers, schools, and so forth).

In one or more embodiments of the invention, a data repository (125) is configured to store data associated with the physician recommendation system (110). The data repository (125) may be any sort of system capable of storing data, such as a relational database, a database management system, a hierarchical file, a flat file, etc. The data repository (125) may be directly connected with the physician recommendation system (110), or through various network configurations (e.g. wired, wireless, LAN, WAN).

Figure 2:
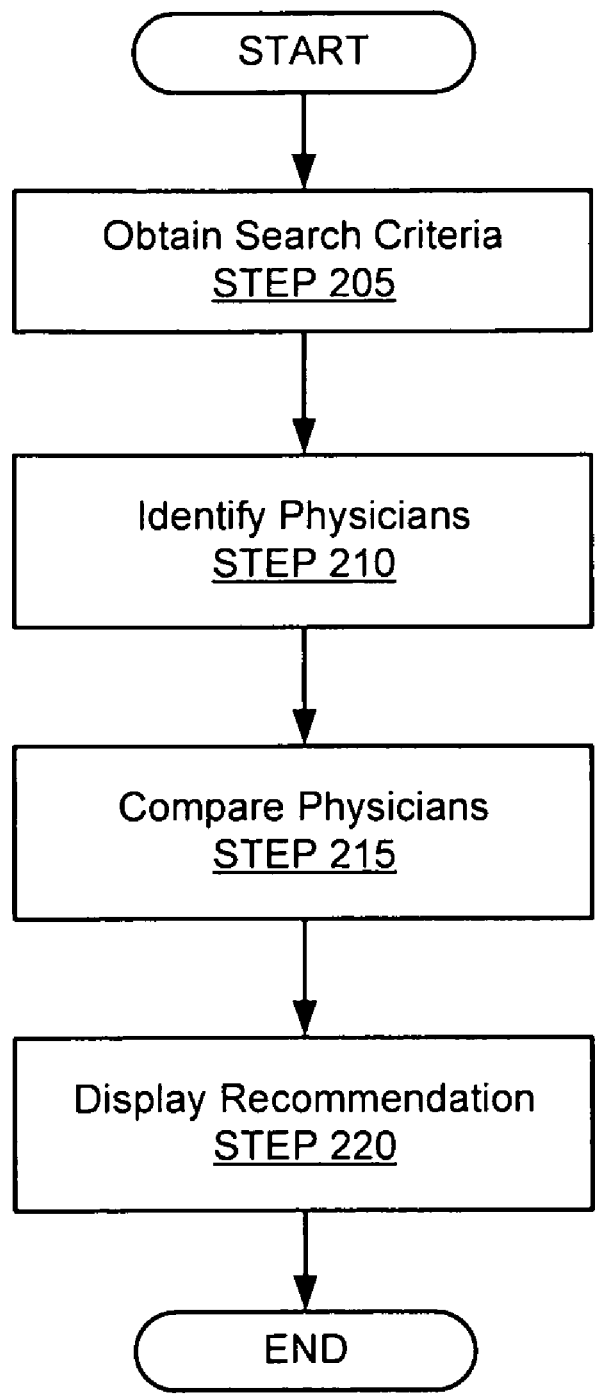
FIGS. 2 and 3 show flowcharts of a method in accordance with one or more embodiments of the invention.

FIG. 2 shows a flowchart in accordance with one or more embodiments of the invention. The process shown in FIG. 2 may be used, for example, with the system (110 of FIG. 1), for recommending a physician based on user generated content. Those skilled in the art, having the benefit of this detailed description, will appreciate that the sequence of steps shown in FIG. 2 may differ among embodiments of the invention, and that one or more of the steps may be optional.

In STEP 205, search criteria is obtained. In one or more embodiments of the invention, the search criteria is obtained from a user. Primary search criteria may include how many patients have seen a specific physician within a specific time period (e.g. the last year), how many patients specified a physician as their favorite physician, a physician's specialty (e.g. PCP, pediatrician, neurologist, orthopedic surgeon), a physician's location, a physician location range from a user (e.g. within 5 miles), accepting new patients (e.g. yes), experience with a particular medical procedure (e.g. radiofrequency ablation, MAZE procedure), experience treating a particular medical condition (e.g. atrial fibrillation, bradycardia, tachycardia), experience treating patients of a particular age (e.g. over 50), experience treating patients of a particular gender (e.g. females), group practice (e.g. PAMF), education (e.g. degrees, names of institutions, locations, years of graduations, ranking within institutions), credentials (e.g. board certifications, special awards, honors), gender (e.g. female), languages spoken (e.g. English & Spanish), office hours (e.g. after 5 PM), a physician's age (e.g. less than 60), and a physician's application of alternative medicine (e.g. active). Secondary search criteria may also be obtained, to further refine a search beyond the primary search criteria. Secondary search criteria may include subspecialty (e.g. pediatric Ear-Nose-Throat (ENT), pediatric behavioral disorders), experience details (e.g. name of procedures performed, name of conditions treated, treated patients ages and genders), and further educational details (e.g. medical schools by rank, Ph.D., J.D., etc.).

Continuing with FIG. 2, physicians are identified (STEP 210). In one or more embodiments of the invention, physicians may be identified by the physician recommendation system (110 of FIG. 1). A results list of physicians may be presented to a user, based on a ranking of user physician experience data according to the criteria specified by a user. The results may be ordered, with the highest ranking physician as the first entry, and the lowest ranking physician as the last entry. Those skilled in the art, having the benefit of this detailed description, will appreciate that various ways exist in which physicians are identified, ranked, and displayed.

Continuing with FIG. 2, physicians are compared (STEP 215). In one or more embodiments of the invention, the physicians may be compared by the physician recommendation system (110 of FIG. 1). A user may compare two or more physicians in a side-by-side view. A user may review information that is likely to help him/her decide between physicians (e.g. experience, subspecialty, photo, physician's personal statement, location, and office hours), as well as information regarding appointments. Those skilled in the art, having the benefit of this detailed description, will appreciate that there will be various manners in which a user may compare physicians. After comparing physicians, a user may select a physician from the list of physicians being compared.

Continuing with FIG. 2, a recommendation is displayed (STEP 220). In one or more embodiments of the invention, the recommendation may be displayed by the physician recommendation system (110 of FIG. 1) in the browser (105 of FIG. 1). The recommendation reflects the final physician selected by a user from a list of recommendations based on selection criteria. The recommendation may be in the form of a complete physician profile devoted to detailed information about the physician. Additional features included in the physician profile beyond the aforementioned search criteria information may include links to external recommendation systems, as well as a link to search engine results based on the physician's name, map results based on the physician's office location, and the like. Those skilled in the art, having the benefit of this detailed description, will appreciate that there will be many other features associated with a physician profile.

In one or more embodiments of the invention, the physician recommendation system (110 of FIG. 1) may enable patients to streamline the process of finding a physician that suits their needs, and may allow both patients and physicians to reduce time spent in the process of identifying a suitable patient-physician match. It may also allow insurance companies to streamline their expenses. Moreover, revenues may be generated from physician membership fees, consumer membership fees, company licensing, online advertising, as well as partnerships and transactions involving mined user data. Those skilled in the art, having benefit of this detailed description, will appreciate that there will be many other ways in which the system may make the physician identification process more efficient, as well as many other ways through which the system may generate revenue streams.

Figure 3:
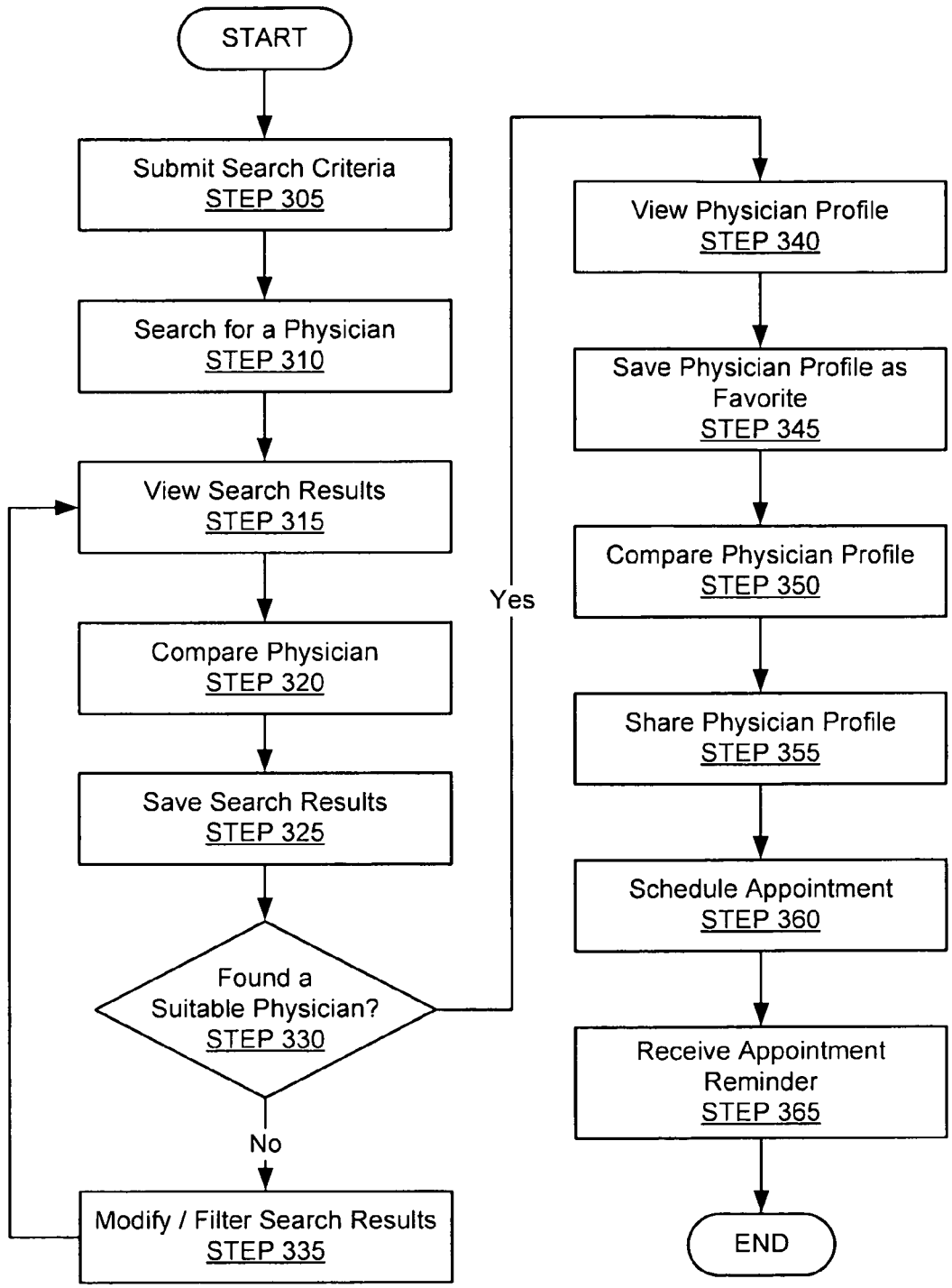

FIG. 3 shows a flowchart in accordance with one or more embodiments of the invention. The process shown in FIG. 3 may be used, for example, with the system (100), for comparing physicians to choose one best suited for an individual's needs. Those skilled in the art, having the benefit of this detailed description, will appreciate that the sequence of steps shown in FIG. 3 may differ among embodiments of the invention, and that one or more of the steps may be optional.

In STEP 305, search criteria is submitted. The search criteria may be submitted by a user. See STEP 205 for details of search criteria. A user may be required to provide login information (e.g. username and password) if he/she attempts to access any features that require recognition of the user (e.g. save searches, favorites, reminders). A user may search for a specific physician if, for example, the user would like to look up information on that specific physician and knows the physician's name or other information. In this case, a user may search based on physician information including last name, first name, location, specialty, and so forth. Additionally, a user may also search for a physician based on a help wizard feature, in which the user would be asked specific questions regarding their preferences for a physician and provide responses to be used as search criteria. Those skilled in the art, having the benefit of this detailed description, will appreciate that there will be many different types of search criteria and mechanisms for many different types of searches beyond what has been described. In one or more embodiments of the invention, user typographical errors are corrected when errors are made within search fields requiring manual entry. For instance, if a user misspells a medical term or a name, a user is prompted whether he/she really meant something else (i.e. a medical term that may have the correct spelling), and submits search criteria according to the user's response in accordance with one or more embodiments of the invention.

Continuing with FIG. 3, a search for a physician is performed (STEP 310). In one or more embodiments of the invention, the search is performed by a user. In such an embodiment, the user submits the search criteria from STEP 305, and physicians are searches for and ranked according to the search criteria. The physicians may be ranked according to the number of times a particular physician has been saved as a favorite physician. Therefore, the highest ranking physician would be the physician that is the most popular among patients or potential patients. Another method of ranking physicians involves filtering recommendations based on users with common attributes. Thus, the highest ranking physician would be one that has been saved as a favorite physician by other users with similar demographic characteristics as a current user searching for a physician. Yet another ranking methodology may include ranking physicians based on the number of times that they are chosen as potential physicians by a user. Additionally, rankings may be based on the number of times a physician has actually been scheduled for appointments with users. Those skilled in the art, having the benefit of this detailed description, will appreciate that there will be many different ranking methodologies that may be employed. After ranking the physicians, a set of ordered results of physicians that best qualify according to the search criteria is produced in accordance with one or more embodiments of the invention.

Continuing with FIG. 3, results for the search performed in STEP 310 are viewed (STEP 315). In one or more embodiments of the invention, the search results are viewed by a user. The search results may be presented in the form of an ordered list of physicians. Display of search results may be limited to a manageable number of items per page (e.g. 5), with GUI navigation to previous and next pages. The display of search results may include the selection criteria information (e.g. group practice) and the physician's photograph. A quick view or rollover feature may enable more information when a user performs a mouse-over on a physician's name or photograph, in the form of a pop up window with additional details. The quick view may include a physician's information including personal statement, address, phone, URL of the physician's website, office hours, and a link to a map of the location of his/her office. Additionally, columns in the results list with numerical data may be sorted high to low or vice versa.

Continuing with FIG. 3, physicians identified from the results of STEP 315 are compared with each other (STEP 320). In one or more embodiments of the invention, comparison of physician is performed by a user. See STEP 215 for details regarding comparing physicians. In STEP 325, the search results are saved. Saving search results may be performed by a user. After completing the search performed in STEP 315, the search results may be saved with a specifying title. The criteria may be stored and ordering of the results in accordance with one or more embodiments of the invention. Saved results can be accessed at a later time, and the saved results are updated with any changes that may occur to the physician's profiles in the time between accesses. Subsequent to STEP 325, the process proceeds to STEP 330.

Continuing with FIG. 3, a determination is made whether a suitable physician is found (STEP 330). If a determination is made that a suitable physician has been identified, then the process proceeds to STEP 340. If a determination is made that a suitable physician has not been identified, then the process proceeds to STEP 335. In STEP 335, it is determined that a suitable physician has not been found, and therefore the search results are modified and/or filtered. The search results may be modified or filtered by a user. In one or more embodiments of the invention, a help link provides advice on how to further sort and filter search results. A description of filtering details may be found in STEP 205. Subsequently the process returns to STEP 315. In STEP 340, it is determined that a suitable physician has been found, and thus the physician's profile is viewed. The physician's profile may be viewed by a user. A description of a physician profile may be found in STEP 220. Additionally, a 'more like this' feature may provide users with a means for viewing additional physician profiles with similar criteria results.

In STEP 345, the physician's profile is saved as a favorite in accordance with one or more embodiments of the invention. Saving the physician's profile may be performed by a user, and may allow the user to log out of the physician recommendation system (110 of FIG. 1) and later log in and access the saved physician profile from a list of favorite physicians. In one or more embodiments of the invention, users annotate or tag comments to a physician's profile in their favorite list.

Continuing with FIG. 3, the physician's profile is compared with another physician's profile (STEP 350). In one or more embodiments of the invention, the comparison of physician profiles is performed by a user. A description of a physician comparison may be found in STEP 215.

In STEP 355, the physician's profile is shared. In one or more embodiments of the invention, sharing the physician's profile is performed by a user. A user may email or text message a physician's profile to another user or another doctor, for recommendation or suggestion of a specialty provider. The user may attach personal comments through the email or text messaging system. Those skilled in the art, having the benefit of this detailed description, will appreciate that there will be many ways in which a user may share a physician's profile with other users, and that this feature is not limited to email or text messaging.

In STEP 360, an appointment is scheduled. In one or more embodiments of the invention, the scheduling of an appointment is performed by a user. A user may have located a physician that fulfills their needs, and now schedules an appointment. The user would accept a date and time for an available appointment with the physician, and select whether to be reminded by email, phone, or text message, providing such information as appropriate.

In STEP 365, an appointment reminder is received. In one or more embodiments of the invention, the appointment reminder is received by a user at a predetermined time before an appointment. By noting the difference between the date of the reminder and the date of the appointment, the average wait time may be determined in an effort to obtain an appointment with a specific physician. Various other metrics may similarly be mined from the user data. Additionally, after the scheduled appointment date the user may be sent a follow-up message requesting user feedback on the physician appointment.

Figure 4:
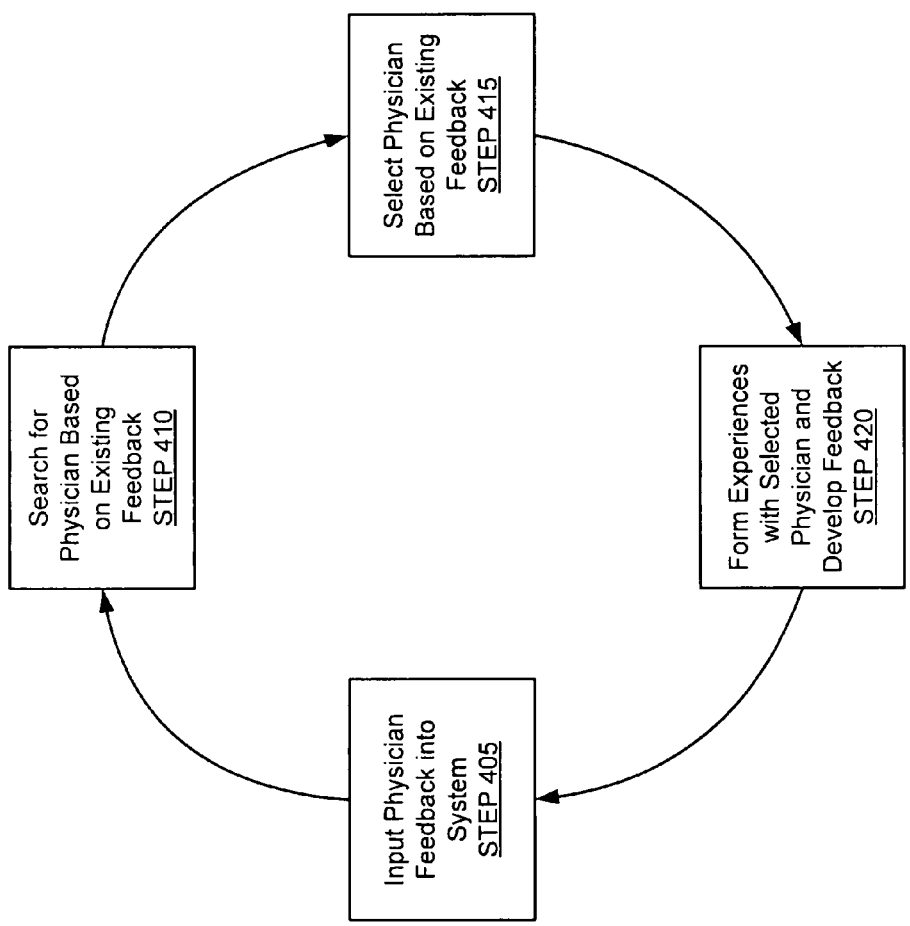
FIGS. 4 and 5 show examples in accordance with one or more embodiments of the invention.

In FIG. 4, an exemplary user feedback loop is demonstrated. Those skilled in the art, having the benefit of this detailed description, will appreciate that the sequence of steps shown in FIG. 4 may differ among embodiments of the invention, and that one or more of the steps may be optional.

In STEP 405, physician feedback is input into the physician recommendation system (110 of FIG. 1) in accordance with one or more embodiments of the invention. The input may be based on previous experiences with a specific physician, and may reveal both positive and negative aspects of those experiences (e.g. physician was very easy to work with, physician did not discuss concerns of patient sufficiently, etc.). The experiences may relate to a specific medical condition, or may be very broad in nature (e.g. during a radiofrequency catheter ablation procedure, physician A achieved sufficient transmural lesions such that patient B did not have to return for a second procedure, physician is generally friendly, etc.). Additionally, implicit feedback may be provided by a user of the system. Implicit feedback may be the actions performed by a user in the physician recommendation system (110 of FIG. 1) relating to interactions with physicians and their profiles. Implicit feedback may be captured by the physician recommendation system (110 of FIG. 1), and may be considered data mining of a user's actions within the physician recommendation system (110 of FIG. 1). Recommendations may then be generated based on implicit user feedback. In this way, user generated content provides the system with data with which to aggregate.

Continuing with FIG. 4, a search for physicians based on existing feedback is performed (STEP 410). The search may include specific criteria such as type of practice, sub specialty, years of practice, educational background, ease of interaction, efficacy of procedures, general ratings, and the like. A search may also be associated with a specific medical condition or a specific treatment. See the description of STEP 205 for more details on search criteria. The results of the search are user generated comments and data based on experiences of previous patients of those physicians. In this way, user generated data is used to recommend a set of physicians.

In STEP 415, a selection of a physician is performed based on existing feedback. The selection may be performed by a user of the system. Once the results to the search of STEP 410 are received, a user may select a physician from those recommended by other previous patients. The selection may be based on a further refined search of the first round of search results, with increasingly specified criteria (e.g. physician must be within 50 miles of a certain location, physician must be of a certain health care provider, and so forth). In this way, user generated data is used to select a final physician (i.e. a final physician is recommended).

In STEP 420, experiences are formed with selected physicians, and feedback on those physicians is developed. The experiences may be formed and feedback developed by a user of the system. This feedback occurs after the recommendation of a physician is made to a user. Prior to visiting the selected physician, a user may also make an appointment with that physician, and receive a reminder for the appointment made with the physician. In this way, user generated content based on experience with a physician is developed, which will further be input into the system as demonstrated in STEP 405. The process proceeds in such a fashion, and the more user generated content is input, the more efficient it becomes at generating targeted and relevant physician recommendations for a user.

Figure 5:
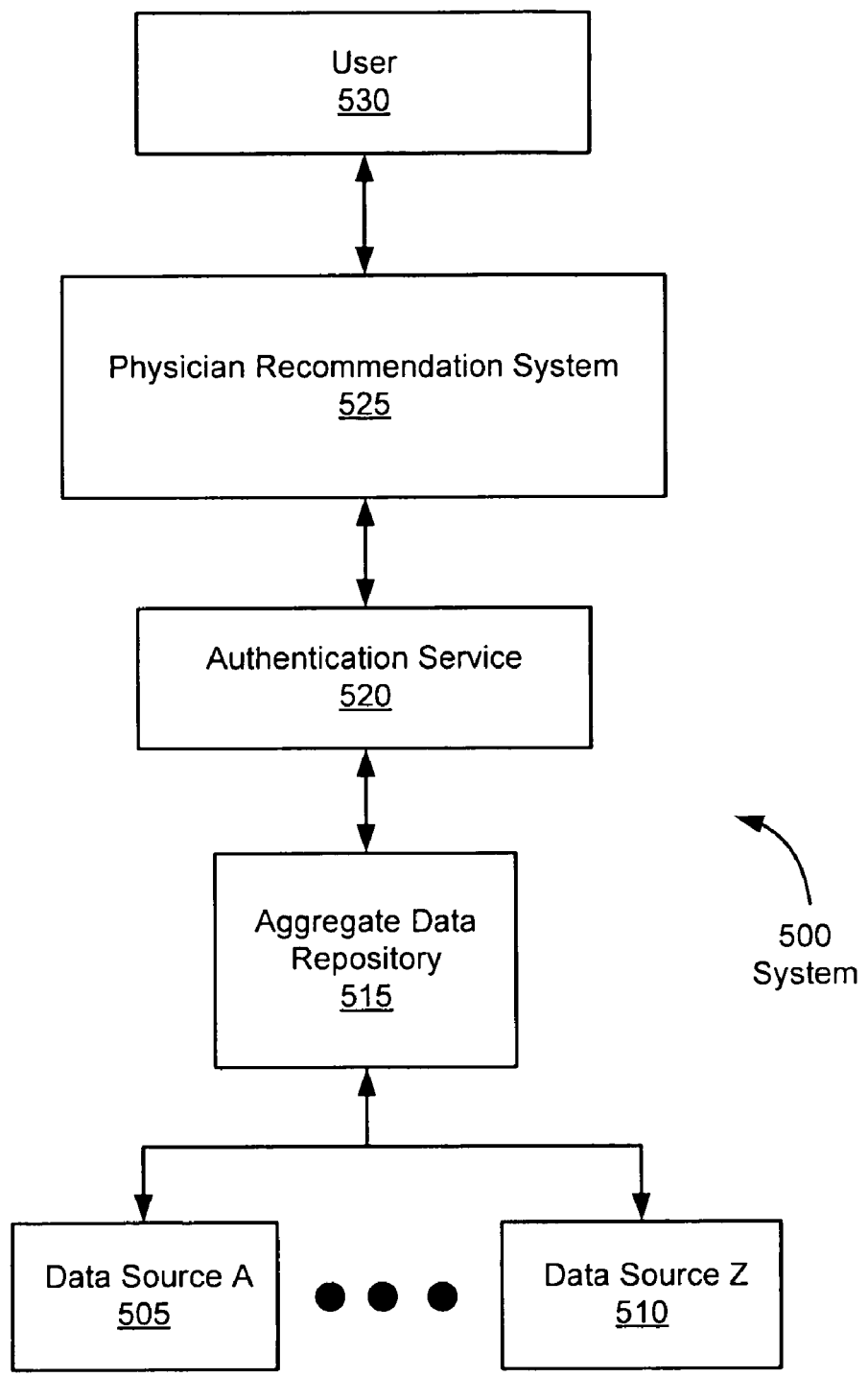

FIG. 5 shows an example of system (500) in accordance with one or more embodiments of the invention. As shown in FIG. 5, the system (500) has multiple components including a multiple data sources (e.g. data source A (505) and data source Z (510)), an aggregate data repository (515), an authentication service (520), a physician recommendation system (525), and a user (530).

In one or more embodiments of the invention, data sources A (505) and Z (510) are configured to provide data to an aggregate data repository (515). The aggregate data repository (515) is configured to store aggregated data from the data sources. For the purposes of this discussion, "aggregated" means "grouped together". For example, if the aggregate data repository (515) is a database, data from the data sources may be grouped together in one or more tables of the database. Alternatively, aggregated data may be grouped together as cells in a spreadsheet, fields of an extensible markup language (XML) document, or in any other aggregated format. Those skilled in the art, having benefit of this detailed description, will appreciate that data may be stored and aggregated in many different ways.

In one or more embodiments of the invention, the data sources (e.g. data source A (505) and data source Z(510)) include one or more users of the physician recommendation system (525) (e.g. potential patients searching for recommendations for physicians). Data from the data sources may include information about the users, such as name, address, healthcare information, and information about a particular physician associated with the user (e.g. physician's name, physician's address, physician's practice area), as well as user comments on experiences with a physician. See the description of STEP 205 for more details regarding data. In one or more embodiments of the invention, users may upload data to one or more aggregate data repositories associated with the data sources.

In one or more embodiments of the invention, an authentication service (520) is configured to restrict access to the aggregate data repository (515). Specifically, the authentication service (520) is configured to ensure that only authorized users are given access to the aggregate data repository (515) through the physician recommendation system (525). For example, the authentication service (520) may require a user to present a username and/or password, an encrypted digital signature, or any other type of authorization credential recognized as valid by the authentication service (520). Additionally, the authentication service (520) may remove or restrict access to identifying or personal information in the aggregate data repository (515) before allowing access to a user (530). In one or more embodiments, the aggregate data repository (515) is located in a local area network (LAN) and the authentication service (520) includes a firewall protecting the LAN from unauthorized access.

In one or more embodiments of the invention, a physician recommendation system (525) is configured to provide recommendations on physicians to users. See the description of FIG. 1 for more details regarding the physician recommendation system (525).

In one or more embodiments of the invention, a user (e.g. a physician) may request information (e.g. patient transfer details) about another user (e.g. a patient transferring to the physician from another physician) from the physician recommendation system (525).

In view of the above, in one or more embodiments of the invention, the data sources may be thought of as input for the aggregate data repository (515), because the data sources are used to input data to the aggregate data repository (515). Further, in one or more embodiments of the invention, the physician recommendation system (525) may be thought of as output for the aggregate data repository (515), because the physician recommendation system (525) generates output based on the data in the aggregate data repository (515). Specifically, the physician recommendation system (525)

generates output in the form of data for users (530), and may also be configured to generate other types of output based on data from the aggregate data repository (515). In one or more embodiments of the invention, the aggregate data repository (515) is communicatively coupled with application programming interfaces (APIs) and GUIs (not shown) that allow input services and/or output services to interact with the aggregate data repository (515).

Figure 6:
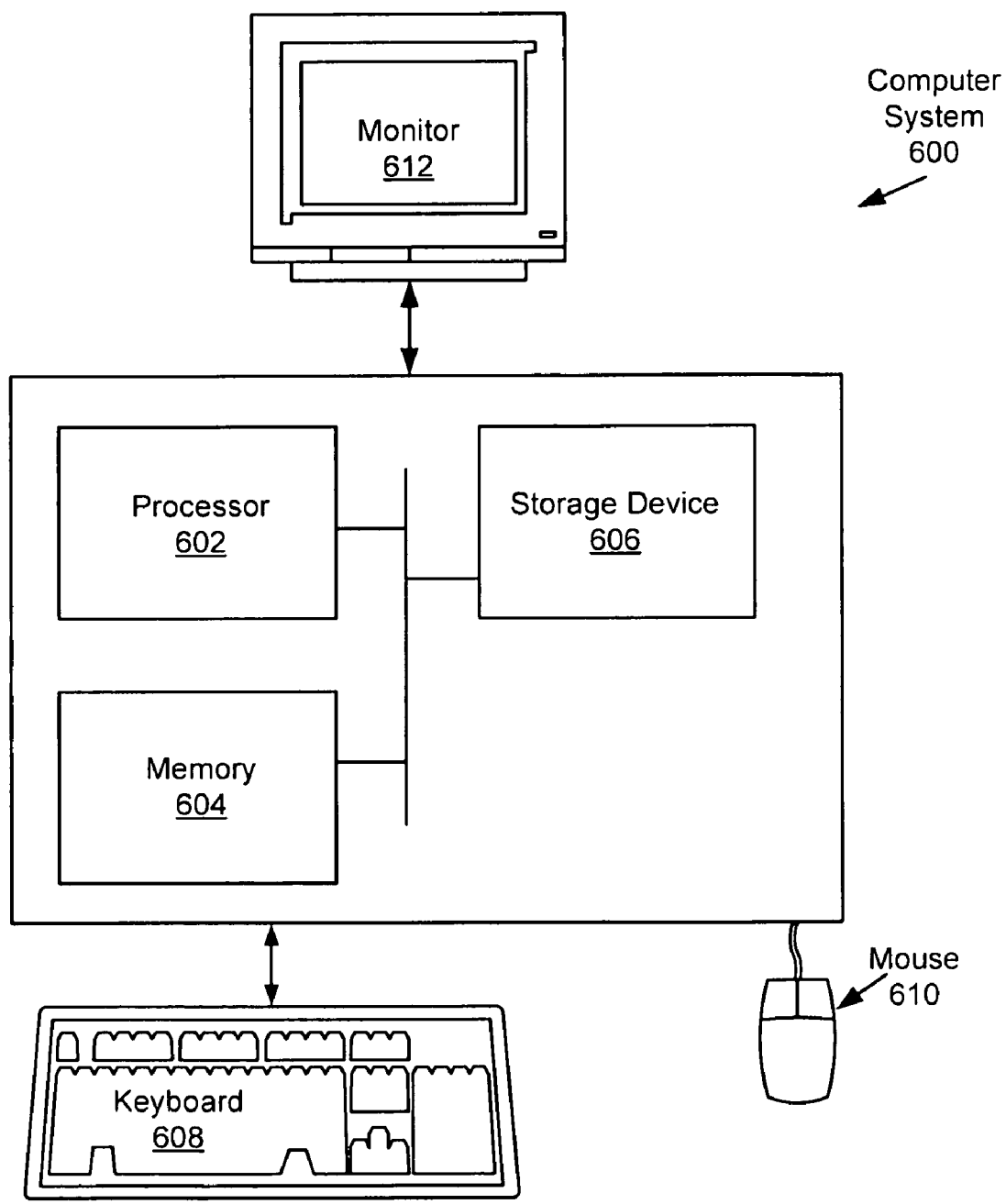
FIG. 6 shows a diagram of a computer system in accordance with one or more embodiments of the invention.

Embodiments of the invention may be implemented on virtually any type of computer regardless of the platform being used. For example, as shown in FIG. 6, a computer system (600) includes one or more processor(s) (602), associated memory (604) (e.g., random access memory (RAM), cache memory, flash memory, etc.), a storage device (606) (e.g., a hard disk, an optical drive such as a compact disk drive or digital video disk (DVD) drive, a flash memory stick, etc.), and numerous other elements and functionalities typical of today's computers (not shown). The computer system (600) may also include input means, such as a keyboard (608), a mouse (610), or a microphone (not shown). Further, the computer system (600) may include output means, such as a monitor (612) (e.g., a liquid crystal display (LCD), a plasma display, or cathode ray tube (CRT) monitor). The computer system (600) may be connected to a network (not shown) (e.g., a local area network (LAN), a wide area network (WAN) such as the Internet, or any other similar type of network) with wired and/or wireless segments via a network interface connection (not shown). Those skilled in the art will appreciate that many different types of computer systems exist, and the aforementioned input and output means may take other forms. Generally speaking, the computer system (600) includes at least the minimal processing, input, and/or output means necessary to practice embodiments of the invention.

Further, those skilled in the art will appreciate that one or more elements of the aforementioned computer system (600) may be located at a remote location and connected to the other elements over a network. Further, embodiments of the invention may be implemented on a distributed system having a plurality of nodes, where each portion of the invention (e.g., various modules and/or components shown in FIG. 1 and described above) may be located on a different node within the distributed system. In one embodiment of the invention, the node corresponds to a computer system. Alternatively, the node may correspond to a processor with associated physical memory. The node may alternatively correspond to a processor with shared memory and/or resources. Further, software instructions for performing embodiments of the invention may be stored on a computer readable medium such as a compact disc (CD), a diskette, a tape, a file, or any other computer readable storage device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for generating a physician recommendation, comprising:

obtaining, using a computer processor and from a first patient, a first patient feedback for a first physician and a second physician wherein the first patient feedback indicates that the first physician is a favorite physician of the first patient, as specified by said first patient;

obtaining, using the computer processor and from a second patient, a second patient feedback for the first physician and the second physician, wherein the second patient feedback indicates that the first physician is the favorite physician of the second patient; as specified by the second patient;

receiving, using the computer processor and from a third patient, a medical condition criterion specifying a medical condition of the third patient;

searching, using the computer processor and the medical condition criterion, a plurality of physicians to identify the first physician and a second physician, wherein the first physician and the second physician specialize in treating the medical condition;

ranking, using the computer processor, the first physician with a first rank and the second physician with a second rank, wherein the first rank and the second rank are based on the first patient feedback and the second patient feedback, and wherein the first rank exceeds the second rank; and wherein the feedback comprises the first and second patients specifying experiences with said first and second physicians related to the medical condition;

generating, using the computer processor, the physician recommendation for the first physician based on the first rank exceeding the second rank.

2. The method of claim 1, further comprising:

wherein the feedback obtained from the first patient for the second physician includes a first medical procedure feedback for the second physician, wherein the first medical procedure feedback indicates that the second physician successfully performed a medical procedure on the first patient;

wherein the feedback obtained from the first patient for the first physician includes a first medical procedure feedback for the first physician;

wherein the feedback obtained from the second patient for the second physician includes a second medical procedure feedback for the second physician, wherein the second medical procedure feedback indicates that the second physician successfully performed the medical procedure on the second patient;

wherein the feedback obtained from the second patient for the first physician includes a second medical procedure feedback for the first physician;

receiving, from the third patient, a medical procedure criteria specifying the medical procedure to be performed on the third patient;

searching, using the medical procedure criteria, the plurality of physicians to identify the first physician and the second physician, wherein the first physician and the second physician specialize in performing the medical procedure;

ranking the first physician with a first medical procedure rank and the second physician with a second medical procedure rank, wherein the first medical procedure rank and the second medical procedure rank are based on the first medical procedure feedback and the second medical procedure feedback, and wherein the second physician medical procedure rank exceeds the first physician medical procedure rank; and generating the physician recommendation for the second physician based on the second rank exceeding the first rank.

3. The method of claim 1, further comprising:
displaying a profile of the second physician after generating the physician recommendation; and storing the profile.

4. The method of claim 3, further comprising:
identifying the profile as a favorite profile of the first patient;
receiving, from the first patient, a request to store the profile as the favorite profile;
adding the favorite profile to a list of favorite profiles of the first patient; and
storing the favorite profile.

5. The method of claim 3, further comprising:
receiving, from the first patient, a request to share the profile with the second patient; and
sharing the profile with the second patient by emailing the profile to the second patient.

6. The method of claim 1, further comprising:
receiving, from the first patient, a request to schedule an appointment with the first physician; and
scheduling the appointment with the first physician.

7. The method of claim 6, further comprising:
calculating a number of days between a current date and a calendar date of the appointment;
determining that the number of days is less than a threshold;
generating, in response to the number of days being less than the threshold, a reminder text message for the appointment with the first physician plurality of physicians; and
transmitting the reminder text to the first patient through a mobile device.

8. The method of claim 1, further comprising:
displaying, to the first patient, a plurality of questions related to the first physician
receiving a plurality of answers to the plurality of questions from the first patient; and
updating a profile of the first physician using the plurality of answers from the first patient.

9. The method of claim 1, further comprising:
determining that the first physician is not available;
generating, in response to the first physician not being available, a secondary physician recommendation for the second physician; and
displaying the secondary physician recommendation.

10. The method of claim 1, wherein the first patient feedback further comprises a comment by the first patient on an experience with the first physician following a submission of an insurance claim.

11. The method of claim 1, wherein the first patient feedback is associated with a financial application.

12. The method of claim 1, further comprising:
searching, using an alternative medicine criteria, the plurality of physicians to identify the first physician and the second physician, wherein the first physician and the second physician practice alternative medicine.

13. The method of claim 1, further comprising:
searching, using a total patients treated criteria, the plurality of physicians to identify the first physician and the second physician, wherein the first physician has treated a first number of patients in a time period, and the second physician has treated a second number of patients in the time period.

14. A system for generating a physician recommendation, comprising:
a processor; and
a physician recommendation system executing on the processor resident in memory and configured to:
obtain, from a first patient, a first patient feedback for a first physician and a feedback for a second physician wherein the first patient feedback indicates that the first physician is a favorite physician of the first patient, as specified by the first patient;
obtain, from a second patient, a second patient feedback for the first physician and the second physician, wherein the second patient feedback indicates that the first physician is the favorite physician of the second patient, as specified by the second patient;
receive, from a third patient, a medical condition criterion specifying a medical condition of the third patient;
search, using the medical condition criterion, a plurality of physicians to identify the first physician and a second physician, wherein the first physician and the second physician specialize in treating the medical condition;
rank the first physician with a first rank and the second physician with a second rank, wherein the first rank and the second rank are based on the first patient feedback and the second patient feedback, and wherein the first rank exceeds the second rank; and
wherein the feedback comprises the first and second patients specifying experiences with said first and second physicians related to the medical condition;
generate the physician recommendation for the first physician based on the first rank exceeding the second rank.

15. The system of claim 14, wherein the physician recommendation system is further includes:
wherein the feedback obtained from the first patient for the second physician includes a first medical procedure feedback for the second physician, wherein the first medical procedure feedback indicates that the second physician successfully performed a medical procedure on the first patient;
wherein the feedback obtained from the first patient for the first physician includes a first medical procedure feedback for the first physician;
wherein the feedback obtained from the second patient for the second physician includes a second medical procedure feedback for the second physician, wherein the second medical procedure feedback indicates that the second physician successfully performed the medical procedure on the second patient;
wherein the feedback obtained from the second patient for the first physician includes a second medical procedure for the first physician;
receiving, from the third patient, a medical procedure criteria specifying the medical procedure to be performed on the third patient;
searching, using the medical procedure criteria, the plurality of physicians to identify the first physician and the second physician, wherein the first physician and the second physician specialize in performing the medical procedure;
ranking the first physician with a first medical procedure rank and the second physician with a second medical procedure rank, wherein the first medical procedure rank and the second medical procedure rank are based on the first medical procedure feedback and the second medical procedure feedback, and wherein the second physician medical procedure rank exceeds the first physician medical procedure rank; and generating the physician recommendation for the second physician based on the second rank exceeding the first rank.

16. The system of claim 14, wherein the physician recommendation system is further configured to:
display a profile of the second physician after generating the physician recommendation; and store the profile.

17. The system of claim 14, wherein the physician recommendation system is further configured to:
receive, from the first patient, a request to schedule an appointment with the first physician; and
schedule the appointment with the first physician.

18. The system of claim 17, wherein the physician recommendation system is further configured to:
calculate a number of days between a current date and a calendar date of the appointment;
determine that the number of days is less than a threshold;
generate, in response to the number of days being less than the threshold, a reminder text message for the appointment with the first physician; and
transmit the reminder text to the first patient through a mobile device.

19. The system of claim 14, wherein the physician recommendation system is further configured to:
determine that the first physician is not available;
generate, in response to the first physician not being available, a secondary physician recommendation for the second physician; and
display the secondary physician recommendation.

20. The system of claim 14, wherein the physician recommendation system is further configured to remove identifying information of the first patient from the first patient feedback before generating the physician recommendation.

21. A non-transitory computer readable storage medium storing instructions for generating a physician recommendation, the instructions comprising functionality to:
obtain, from a first patient, a first patient feedback for a first physician and a second physician wherein the first patient feedback indicates that the first physician is a favorite physician of the first patient, as specified by the first patient;
obtain, from a second patient, a second patient feedback for the first physician and the second physician, wherein the second patient feedback indicates that the first physician is the favorite physician of the second patient; as specified by the second patient;
receive, from a third patient, a medical condition criterion specifying a medical condition of the third patient;
search, using the medical condition criterion, a plurality of physicians to identify the first physician and a second physician, wherein the first physician and the second physician specialize in treating the medical condition;
rank the first physician with a first rank and the second physician with a second rank, wherein the first rank and the second rank are based on the first patient feedback and the second patient feedback, and wherein the first rank exceeds the second rank;
wherein the feedback comprises the first and second patients specifying experiences with said first and second physicians related to the medical condition; and
generate the physician recommendation for the first physician based on the first rank exceeding the second rank.

22. The non-transitory computer readable storage medium of claim 21, further including:
wherein the feedback obtained from the first patient for the second physician includes a first medical procedure feedback for the second physician, wherein the first medical procedure feedback indicates that the second physician successfully performed a medical procedure on the first patient;
wherein the feedback obtained from the first patient for the first physician includes a first medical procedure feedback for the first physician;
wherein the feedback obtained from the second patient for the second physician includes a second medical procedure feedback for the second physician, wherein the second medical procedure feedback indicates that the second physician successfully performed the medical procedure on the second patient;
wherein the feedback obtained from the second patient for the first physician includes a second medical procedure for the first physician;
receiving, from the third patient, a medical procedure criteria specifying the medical procedure to be performed on the third patient;
searching, using the medical procedure criteria, the plurality of physicians to identify the first physician and the second physician, wherein the first physician and the second physician specialize in performing the medical procedure;
ranking the first physician with a first medical procedure rank and the second physician with a second medical procedure rank, wherein the first medical procedure rank and the second medical procedure rank are based on the first medical procedure feedback and the second medical procedure feedback, and wherein the second physician medical procedure rank exceeds the first physician medical procedure rank; and
generating the physician recommendation for the second physician one of the refined plurality of physicians based on the second rank exceeding the first rank.

23. The non-transitory computer readable storage medium of claim 21, the instructions further comprising functionality to:
display a profile of the second physician after generating the physician recommendation; and
store the profile.

24. The non-transitory computer readable storage medium of claim 23, the instructions further comprising functionality to:
identify the profile as a favorite profile of the first patient;
receive, from the first patient, a request to store the profile as the favorite profile;
add the favorite profile to a list of favorite profiles of the first patient; and
store the favorite profile.

25. The non-transitory computer readable storage medium of claim 23, the instructions further comprising functionality to:
receive, from the first patient, a request to share the profile with the second patient; and
share the profile with the second patient by emailing the profile to the second patient.

26. The non-transitory computer readable storage medium of claim 21, the instructions further comprising functionality to:
display, to the first patient, a plurality of questions related to the first physician
receive a plurality of answers to the plurality of questions from the first patient; and update a profile of the first physician using the plurality of answers from the first patient.

27. The non-transitory computer readable storage medium of claim 21, the instructions further comprising functionality to:
    determine that the first physician is not available;
    generate, in response to the first physician not being available, a secondary physician recommendation for the second physician; and
    display the secondary physician recommendation.

28. The non-transitory computer readable storage medium of claim 21, wherein the first patient feedback further comprises a comment by the first patient on an experience with the first physician following a submission of an insurance claim.

29. The non-transitory computer readable storage medium of claim 21, the instructions further comprising functionality to:
    search, using an alternative medicine criteria, the plurality of physicians to identify the first physician and the second physician, wherein the first physician and the second physician practice alternative medicine.

30. The non-transitory computer readable storage medium of claim 21, the instructions further comprising functionality to:
    search, using a total patients treated criteria, the plurality of physicians to identify the first physician and the second physician, wherein the first physician has treated a first number of patients in a time period, and the second physician has treated a second number of patients in the time period.

\* \* \* \* \*